United States Patent [19]
Hemstreet et al.

[11] Patent Number: 5,387,191
[45] Date of Patent: Feb. 7, 1995

[54] FLUSHING NEEDLE

[75] Inventors: George P. Hemstreet, Oklahoma City; Tom J. Love, Jr.; Karl H. Bergey, both of Norman, all of Okla.

[73] Assignee: Board of Regents of the Univ. of Okla., Norman, Okla.

[21] Appl. No.: 779,699

[22] Filed: Oct. 21, 1991

Related U.S. Application Data

[60] Division of Ser. No. 602,580, Oct. 24, 1990, Pat. No. 5,081,999, which is a continuation of Ser. No. 307,403, Feb. 6, 1989, Pat. No. 4,982,739.

[51] Int. Cl.$^6$ ............................................. A61M 11/00
[52] U.S. Cl. ...................................... 604/93; 604/131; 604/264; 604/272
[58] Field of Search ....................... 604/22, 27, 30, 48, 604/51, 52, 53, 93, 128, 131, 150, 151, 153, 264, 272; 606/107

[56] References Cited

U.S. PATENT DOCUMENTS 3,477,423 11/1969 Griffith et al. .
3,819,091 6/1974 Hollender et al. .
4,493,694 1/1985 Wuchinich ............................ 604/22

OTHER PUBLICATIONS

W. J. Catalona & W. W. Scott, Carcinoma of the Prostate, Campbell's Urology, 5th ed., vol. 2, pp. 1477–1480 (W. B. Saunders Co. 1986).
The Clinical Cancer Letter, vol. 10, No. 8, Reston, Virginia, Aug. 1987.
Oncology Viewpoints, vol. 2, No. 5, LP Communications, Inc., New York, N.Y., 1988. pp. 4–17.

Primary Examiner—Randy C. Shay
Attorney, Agent, or Firm—Dunlap, Codding & Lee

[57] ABSTRACT

A fine-needle aspirator for collecting a biosample from a subject into a closed sterile system. The aspirator is adapted for use with a variety of needles and comprises a motor driven pump capable of continuous suction in a biosample collection system. The biosample collection system may comprise a biosample connector such as elastomeric tubing in communication with the needle and a collection space in a biosample container whereby a biosample collected by the needle may be transferred to the collection space. A flushing substance flushes the biosample through the biosample collection system. Additives may be added to the biosample after collection in order to treat, preserve or analyze the biosample.

2 Claims, 6 Drawing Sheets

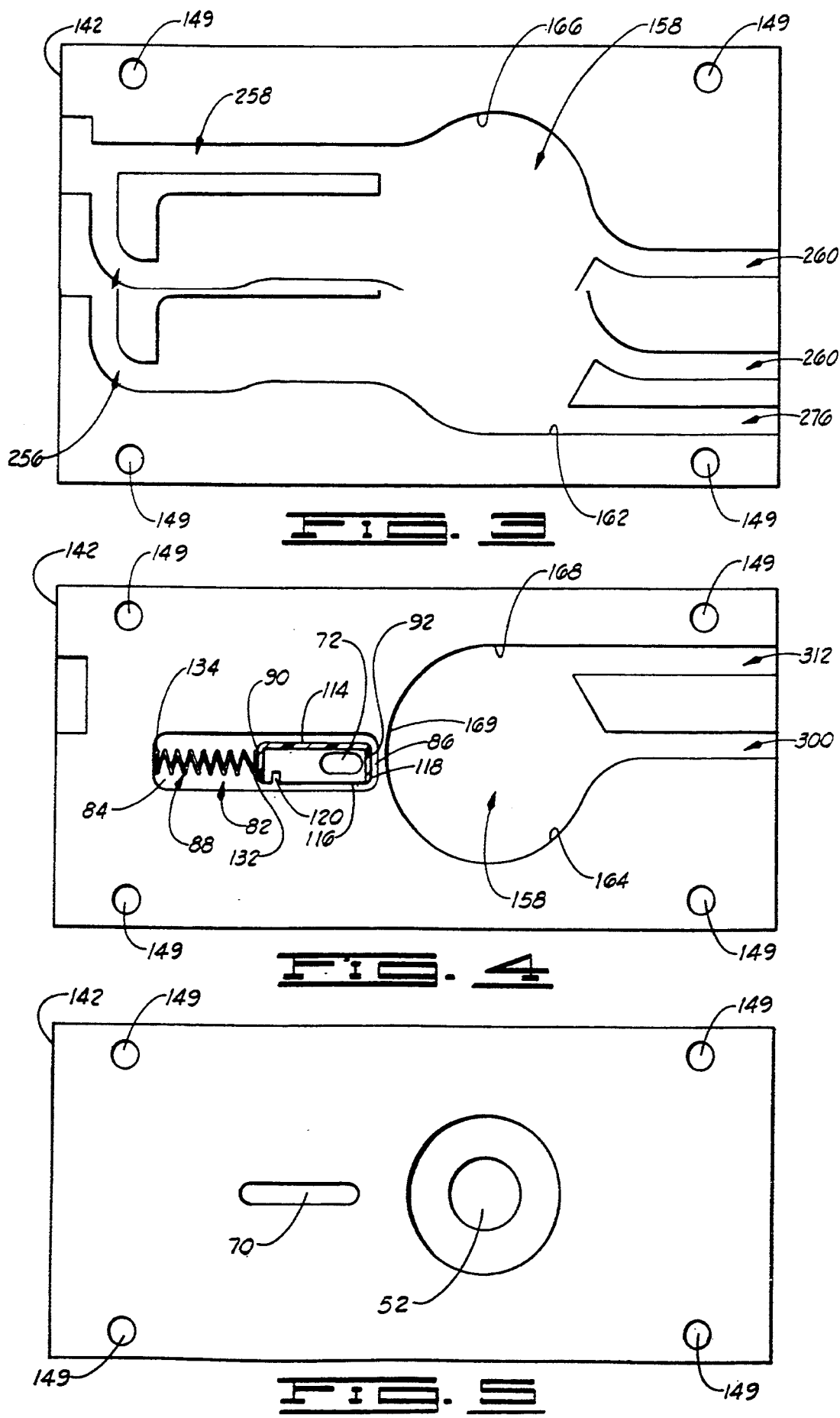

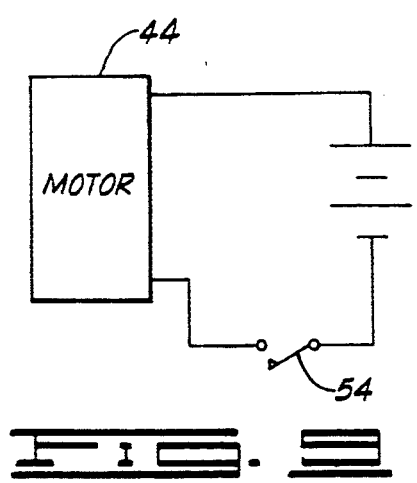
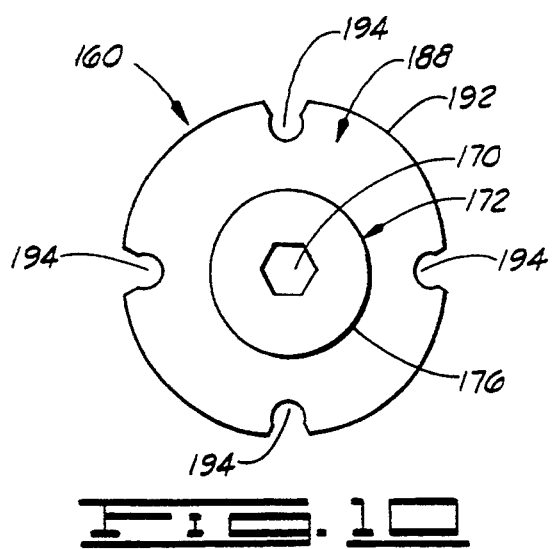
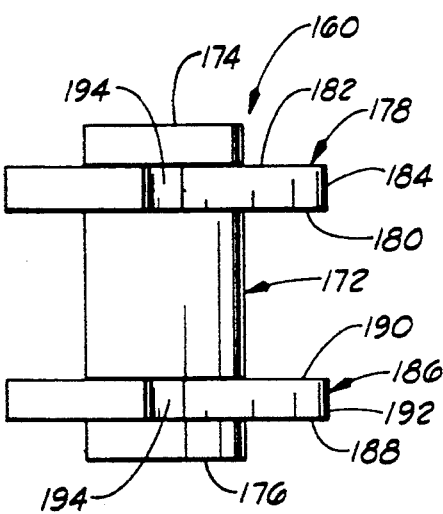
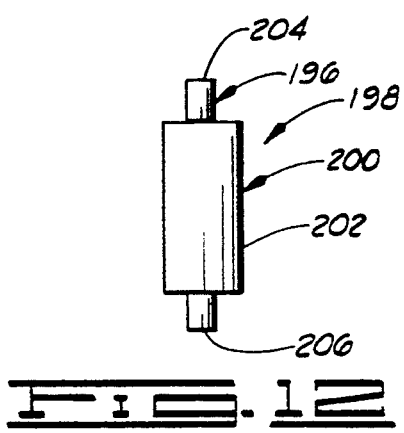
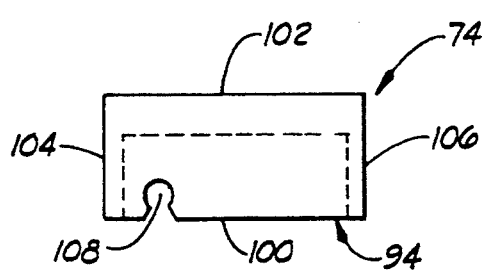
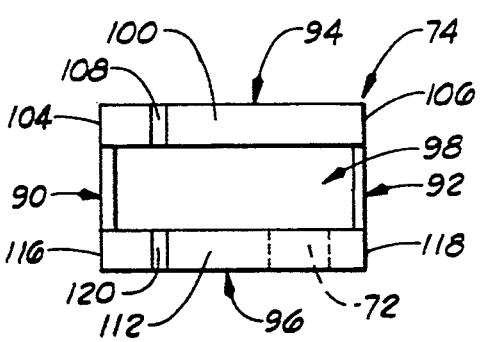
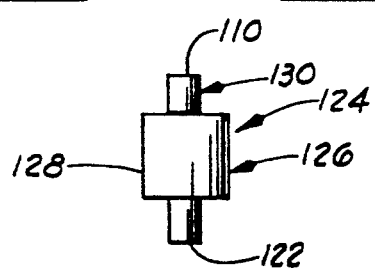

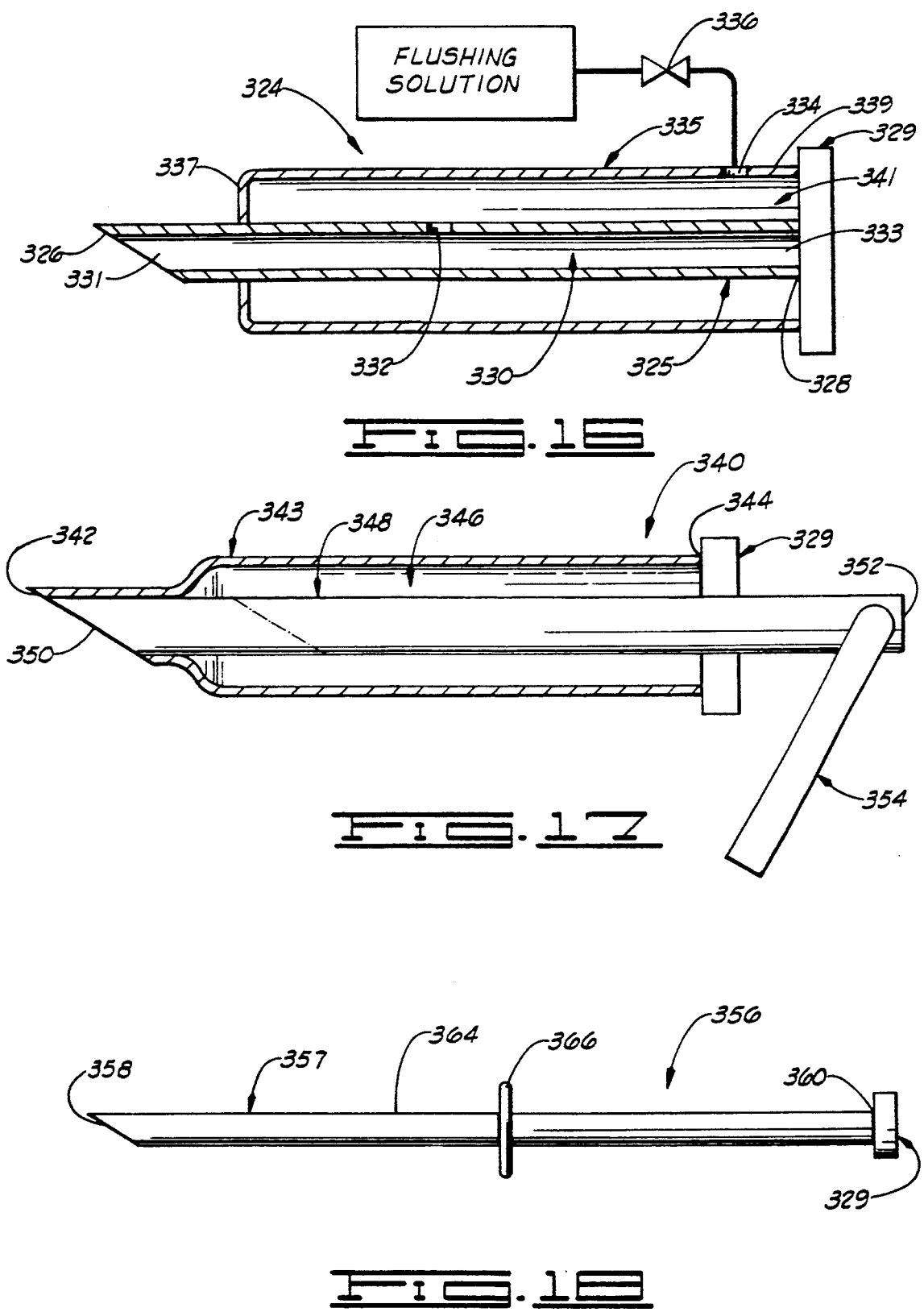

FLUSHING NEEDLE

This application is a division of U.S. Ser. No.: 07/602,580, filed: Oct. 24, 1990, entitled BIOSAMPLE ASPIRATOR, now U.S. Pat. No. 5,081,999, which was a continuation of U.S. Ser. No. 07/307,403, filed Feb. 6, 1989, entitled BIOSAMPLE ASPIRATOR, now U.S. Pat. No. 4,982,739.

FIELD OF THE INVENTION

The present invention relates generally, but not by way of limitation, to methods and devices for obtaining biological samples from a subject.

BRIEF DESCRIPTION OF THE DRAWINGS

FIGS. 2–5 are horizontal cross sections of the pump housing of the present invention. FIG. 5 is the lowest section upon which respectively sections in FIGS. 4, 3 and 2 are mounted.

FIG. 2 is a top plan view of a cross section of the pump housing of the present invention.

FIG. 3 is a top plan view of a cross section of the pump housing of the present invention showing a portion of the pump housing component space.

FIG. 4 is a top plan view of a cross section of the pump housing of the present invention showing a portion of the pump housing component space including a portion of the trigger aperture which contains a slide spring attached to the trigger slide shown in a horizontal cross section and the rod support member space.

FIG. 5 is a top plan view of the lowest cross section of the pump housing of the present invention showing a portion of the trigger aperture and the pump housing shaft aperture.

FIG. 9 is a schematic drawing of the switch of the present invention in the open position.

FIG. 10 is a bottom plan view of the rod support member.

FIG. 11 is an elevational side view of the rod support member.

FIG. 12 is an elevational side view of a rod.

FIG. 13 is a top plan view of the control member guide.

FIG. 14 is a side elevational view of the control member guide.

FIG. 15 is a side elevational view of the control member.

FIG. 16 is a side elevational view of the flushing needle.

FIG. 17 is a side elevational view of the obturator needle.

FIG. 18 is a side elevational view of the flanged needle.

DETAILED DESCRIPTION OF THE PREFERRED EMBODIMENTS

The present invention comprises a fine-needle aspirator adapted for use in collecting a biosample such as fluid or tissue from a subject such as a human into a closed sterile system. The aspirator is adapted to be used with a needle having a first end and a second end with an opening therethrough and comprises a biosample collection system and a suction means.

The suction means generates and establishes a vacuum capable of continuous suction in the biosample collection system whereby a biosample received via the first end of the needle is movably transferred through the needle opening into the biosample collection system. The biosample collection system comprises a biosample collection area and a communicating means for establishing fluidic communication between the needle opening and the biosample collection area. The biosample collection area may be part of the communication means or may comprise a biosample container connected to the communication means having a collection space sized to receive at least one biosample.

Figure 1:
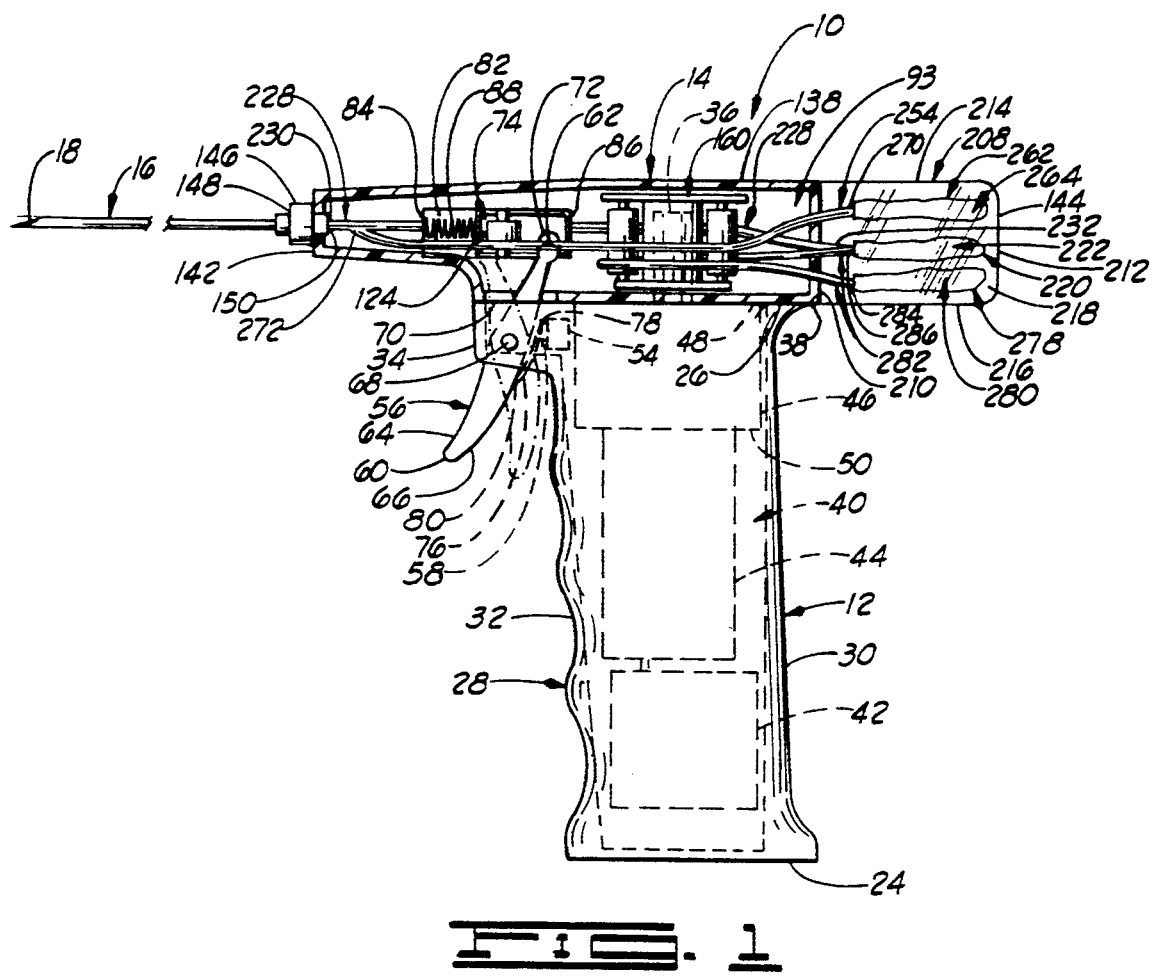
FIG. 1 is a side view in cross section of the biopsy gun constructed according to the present invention.

Referring to the drawings in detail, and particularly FIG. 1, reference character 10 generally designates a biosample aspirator in accordance with the present invention. The aspirator 10 comprises a handle housing generally designated by reference character 12 and a pump housing generally designated by reference character 14. A needle 16 having a first end 18 and a second end (not shown) with an opening (not shown) therethrough is secured to the pump housing 14 as described hereafter.

The handle housing 12 comprises a lower end 24 and an upper end 26 with a front surface 28 and back surface 30. The handle housing 12 is sized to be held by one hand and has a generally rounded or oval cross section. The handle housing front surface 28 has a grip area 32 shaped to be easily gripped by one hand while the handle housing back surface 30 is generally straight. Preferably the front surface 28 of the upper end 26 portion of the handle housing 12 extends a distance from the grip area 32 to form a tapered trigger attachment portion 34. The lower end 24 of the handle housing 12 is generally flat and may be adapted to be received in a recharging unit (not shown) capable of recharging the battery contained within the handle housing 12. The upper end 26 of the handle housing 12 has a shaft opening (not shown) through which a rotatable shaft 36 extends therethrough as described hereafter. The upper end 26 of the handle housing 12 secures the lower end 38 of the pump housing 14. Preferably the upper end 26 of the handle housing 12 is formed so that the pump housing 14 selectively snaps onto and off of the handle housing 12 removably securing same.

A housing component space 40 is formed inside the handle housing 12 and is sized to receive a battery 42, motor 44 and gear box 46. In a preferred embodiment, a battery 42 is disposed near the lower end 24 portion of the handle housing 12 in the component space 40 and is operatively connected to a motor 44 positioned above the battery 42 as shown in FIG. 1 to provide electrical current thereto. Mounted on the motor 44 is a gear box 46 having a upper end 48 and a lower end 50. A rotatable shaft 36 extends a distance from the upper end 48 of the gear box 46 through a shaft opening (not shown) in the upper end 26 of the handle housing 12 and into the pump housing 14 through the pump housing shaft aperture 52 (FIG. 5). The battery, motor and gear box of the cordless screwdriver model #9018 made by Black and Decker of Shelton, Conn. may be used in accordance with the present invention.

The electrical current to the motor 44 is selectively provided by a microswitch 54 having an opened and a closed position interposed between the battery 42 and the motor 44 for establishing electrical continuity therebetween. When the microswitch 54 is in a closed position, electrical continuity between the battery 42 and the motor 44 is established and the motor 44 is in a driven or on condition. Electrical continuity between the motor 44 and the battery 42 is interrupted when the microswitch 54 is in the open position as schematically shown in FIG. 9.

The microswitch 54 is positioned in the handle housing component space 40 near the trigger 56. The microswitch 54 also comprises a microswitch button 58 disposed between the microswitch 54 and the trigger 56 so that the trigger 56, when pressed, can selectively contact the microswitch button 58. Contact of the microswitch button 58 by the trigger 56 conditions the microswitch 54 in the closed position.

The trigger 56 may be secured to either the handle housing 12 or the pump housing 14. In a preferred embodiment shown in FIG. 1, the trigger 56 is pivotally secured to the trigger attachment portion 34 of the handle housing 12. The trigger 56 has a tapered lower end 60, an enlarged ball-shaped upper end 62, an inwardly curved finger surface 64 and an outwardly curved back surface 66. The trigger 56 is pivotally secured at about the middle of the trigger to the trigger attachment portion 34 of the handle housing 12 by a pin 68 through aligned pin holes (not shown) in the trigger attachment portion 34 of the handle housing 12 and the trigger 56. The upper end 62 portion of the trigger 56 is received in the handle housing component space 40 with the upper end of the trigger 56 extending through the lower end 38 of the pump housing 14 through the trigger aperture 70 (FIG. 5) with the upper end 62 of the trigger 56 positioned in the trigger tip opening 72 of the trigger slide 74 (FIG. 4) as described hereafter.

The trigger back surface 66 contacts the microswitch button 58 when the trigger finger surface 64 is pressed towards the front surface 28 of the handle housing 12. A trigger spring 76, having an upper end 78 and a lower end 80, is attached near the microswitch button 58 by the upper end 78 thereof. The lower end 80 thereof extends a distance from the microswitch 54, between the trigger back surface 66 and the microswitch 54 so that when the trigger 56 is pressed the trigger back surface 66 contacts the lower end 80 of the trigger spring 76 thereby compressing the trigger spring 76. When the trigger 56 is no longer pressed, the trigger spring 76 resiliently returns to the decompressed position thereby repositioning the trigger 56 in the off position.

A trigger slide aperture 82 having a first end 84 and a second end 86 is formed in the pump housing component space 93 and sized to receive a trigger slide 74 with attached slide spring 88 in an extended position. Referring to FIGS. 13 and 14, the trigger slide 74 comprises a first end plate 90, a second end plate 92, a top plate 94, a bottom plate 96 and a back plate 98. The top plate has a front end 100, a back end 102, a first end 104 and a second end 106 and comprises a control member opening 108 near the first end 104 portion of the top plate 94 sized to secure the upper end 110 of the control member shaft shown in FIG. 15. The bottom plate 96 has a front end 112, a back end 114, a first end 116, and a second end 118 and comprises a control member opening 120 near the first end 116 portion of the bottom plate 96 sized to secure the lower end 122 control member shaft shown in FIG. 15. The control member openings 108 and 120 are aligned so that the control member, as described hereafter, secured therein is supported in an upright position.

As shown in FIGS. 1 and 4, the bottom plate 96 further comprises a trigger tip opening 72 which removably receives the trigger upper end 62. The top plate 94 and the bottom plate 96 are generally horizontally positioned with a back plate 98 secured therebetween at the back end 102 of the top plate 94 and the back end 114 of the bottom plate 96. A first end plate 84 and the second end plate 86 are in a generally vertical position. Referring to FIG. 14, the first end plate 90 secures the first end 104 of the top plate 94, the first end 116 of the bottom plate 96 and a portion of the back plate 98; the second end plate 92 secures the second end 106 of the top plate 94, the second end 118 of the bottom plate 96 and a portion of the back plate 98.

Figure 7:
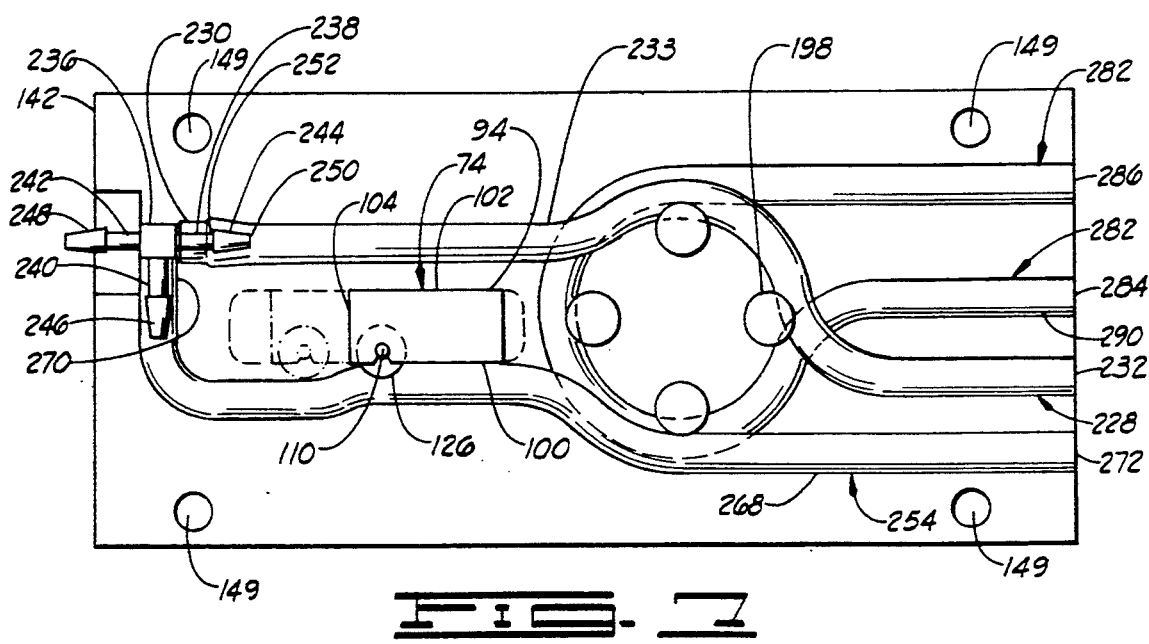
FIG. 7 is a horizontal cross sectional top plan view of a portion of the pump housing of the present invention without the slide spring.

The control member 124 (FIG. 15) comprises a cylinder 126 having an outer periphery 128 rollingly supported on a shaft 130 having an upper end 110 and a lower end 122 extending a distance from each end of the cylinder 126. The upper 110 and lower 122 ends of the control member shaft 130 are respectively secured in the control member opening 108 of the top plate 94 and the control member opening 122 in the bottom plate 96. The control member 124 secured in the trigger slide 74 is thereby selectively positioned to compress the flushing solution connector (interrupt position) or decompress the flushing solution connector (enable position) as shown in FIG. 7 and as described hereafter.

The slide spring 88 has a first end 132 secured to the trigger slide first end plate 90 and a second end 134 secured to the pump housing 14 adjacent to the first end 84 of the trigger slide aperture 82.

In operation, a finger presses the finger surface 64 of the lower end 60 of the trigger 56 towards the handle housing front surface 28 thereby contacting the trigger spring 76 and the microswitch button 58 to establish the on position for the trigger 56. This moves the upper end 62 of the trigger 56 engaged in the trigger tip opening 72 of the trigger slide 74 in the opposite direction thereby compressing the slide spring 88. The control member 124, attached to the trigger slide 74, is thereby positioned so that the flushing solution connector 254 is decompressed and flushing substance may be aspirated therethrough as described hereafter. When the trigger 56 is no longer pressed by the operator, the trigger spring 76 decompresses returning the trigger slide 74 with attached control member 124 and trigger 56 to the original position. Since the microswitch button 58 is no longer contacted, the microswitch 54 is in the open position conditioning the motor in an off position.

The pump housing 14 comprises an upper surface 138, a lower surface 38, a first end 142 and a second end 144. A pump housing component space 93 is formed within the pump housing 14 intersecting the first end 142 and the second end 144. The first end 142 of the pump housing 14 has a needle receiving opening (not shown) to receive a needle 16.

In a preferred embodiment shown in FIG. 1, an annular needle receiving adaptor 146 has a first end 148 and a second end 150 with an opening therethrough (not shown). The adaptor second end 150 portion is secured in the opening of the pump housing first end 142 and secures either a tubing first end 230 as shown in FIG. 1 or a tubular projection 242 with attached shoulder 248 as shown in FIG. 7 and described hereafter. The adaptor first end 148 removably secures aluer lock needle attachment (not shown) secured to the second end of the needle 16.

Figure 2:
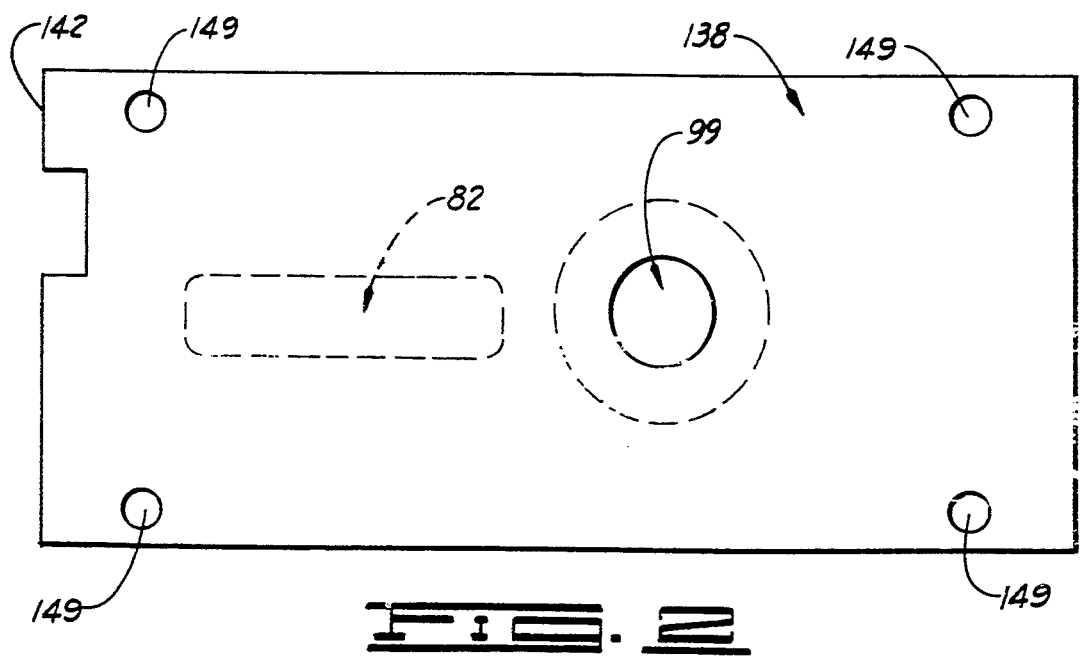
Figure 6:
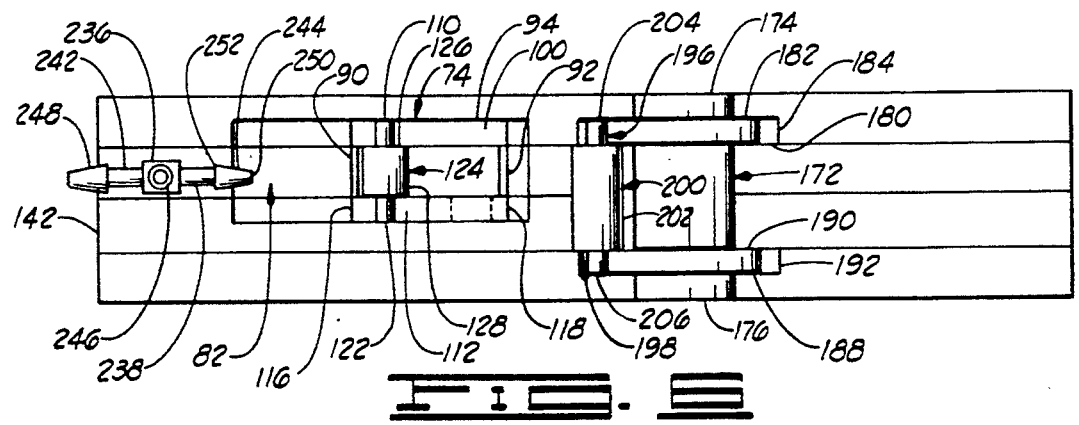
FIG. 6 is a vertical cross sectional view of a portion of the pump housing of the present without the connectors and the slide spring.

FIGS. 2 through 5 show the pump housing 14 in horizontal block cross sections as used in the manufacturing process of a preferred embodiment. These same sections may be shaped to conform to the outer dimensions of the pump housing shown in FIG. 1. FIG. 5 represents the lowest section upon which respectively the sections in FIGS. 4, 3 and 2 are mounted. FIG. 5 shows the pump housing shaft aperture 52 which receives the shaft 36 from the gearbox 46 and the trigger aperture 70 which receives the upper end 62 of the trigger 56. FIG. 2 shows the support post opening 99 which receives the upper end 174 of the support post 172 as described hereafter.

After the appropriate components as described hereafter have been disposed in the pump components space 93, a bolt (not shown) secured in each of the aligned bolt apertures 149 secures the pump housing sections together. The pump housing sections form a pump housing component space 93 which intersects the first end 142 and the second end 144 of the pump housing 14.

A portion of the pump housing component space 93 comprises an eccentrically formed bowl-like rod support member space 158 which receives the rod support member 160 and comprises a continuous first front wall 162 (FIG. 3) and second front wall 164 (FIG. 4), a continuous first back wall 166 (FIG. 3) and second back wall 168 (FIG. 4) and a side wall 169. The space between the outer periphery 192 of the rods 198 of the rod support member 160 and the walls of the rod support member space 158 dictate whether the connectors disposed in that space are contacted by the rod support member 160, i.e., if that space is smaller than the diameter of the connectors the rods of the rod support member will compressingly engage the connectors. This engagement creates a vacuum in the connectors. Thus the shape of the rod support member space selectively controls the amount of contact between the connectors and the rods and therefore the degree of vacuum created in the connectors.

The pump housing component space 93 further comprises a first biosample canal 258 and a second flushing canal 256 that intersect at the first end 142 portion of the pump housing 14 and lead to the rod support member space 158 in about the middle of the pump housing 14. A first flushing canal 276, a second biosample canal 260, an upper additive canal 312 and a lower additive canal 300 lead from the rod support member space 158 to the second end 144 portion of the pump housing 14. The canals 256, 258, 260, 276, 312 and 300 are sized to receive a connector therein as described hereafter.

As previously described, a shaft 36 from the gear box 46 extends into the rod support member space 158 and is engagingly received in the support post aperture 170 of the rod support member 160 (FIG. 11) so that as the shaft 36 rotates, the rod support member 160 rotates. The rod support member 160 comprises a support post 172 having an upper end 174 and a lower end 176. The lower end 176 of the support post 172 has an aperture 170 (FIG. 10) sized to engagingly receive the shaft 36. Preferably the shaft 36 is hexagonal and sized slightly smaller than the hexagonally shaped aperture 170 in the support post 172.

Referring to FIG. 11, the rod support member 160 further comprises an annular upper rod support 178 secured to the upper end 174 portion of the support post 172 having a lower face 180, an upper face 182 and an outer periphery 184, and an annular lower rod support 186 secured to the lower end 176 portion of the support post 172 having a lower face 188, an upper face 190 and an outer periphery 192. The upper rod support 178 and lower rod support 186 include a plurality of rod receiving slots 194 spaced a distance around the periphery 184 and 192 of the rod supports 178 and 186. The slots 194 are shaped and positioned so that a rod shaft 196, as described hereafter, can snap into the slots and be securely supported in an upright position around the rod support member 160.

As shown in FIG. 12, the rod 198 comprises a rod cylinder 200 having an outer periphery 202 rollingly supported on a rod shaft 196 wherein the shaft has an upper end 204 and a lower end 206 which extends a distance from opposite ends of the rod cylinder 200. The upper end 204 of the rod shaft is sized to snap into rod receiving slot 194 in the periphery 202 of the upper rod support 178; the lower end 206 of the rod shaft 196 is sized to snap into the rod receiving slot 194 in the lower rod support 186 thereby securing the rod 198 in an upright position in the rod support member 160. Secured in this manner, the outer periphery 202 of the rod cylinder 200 extends a distance from the rod support member 160 to rollingly engage a portion of the connectors as described hereafter.

In a preferred embodiment, a peristaltic pump comprising four rods 198 secured at equispaced distances in the foregoing manner in the rod support member 160 providing a circular configuration of rotatable rods 198 is utilized in accordance with the present invention. When the motor 44 is in the on position, the shaft 36 rotates which rotates the rod support member 160 having the rods 198 secured thereto. Selected connectors, as described hereafter, are alternately compressed by the rods 198 in a peristaltic movement when the outer periphery 192 of each rod 198 rolls along the connectors thereby compressing the connectors. This engagement of the connectors by the rods 198 creates a vacuum in the connectors and attached needle 16.

Figure 19:
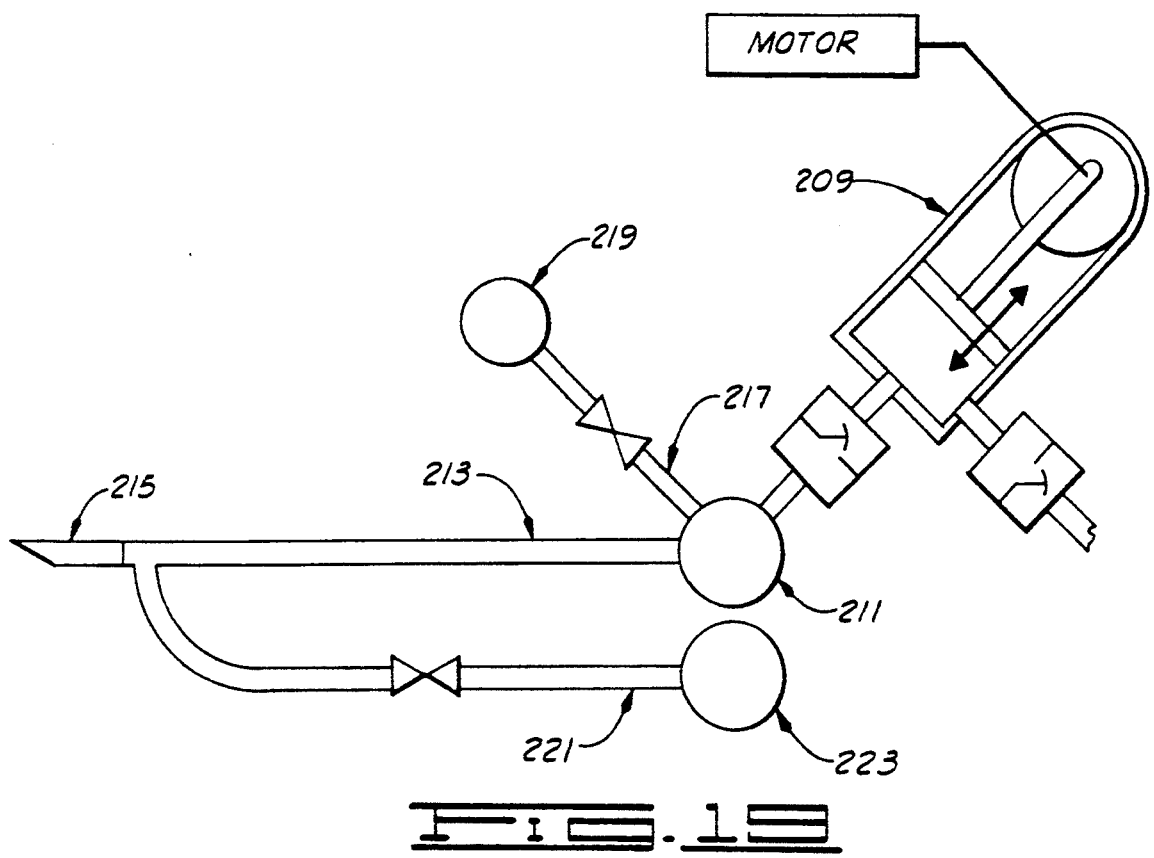
FIG. 19 is a schematic drawing of the aspirator in accordance with the present invention using a piston pump.

Instead of the peristaltic pump described in the foregoing, the present invention may use any other type of pump which appropriately provides the necessary vacuum action in the biosample collection system. FIG. 19 shows an embodiment of the present invention which utilizes a piston pump 209 driven by a motor source. The piston pump 209 produces a vacuum in the biosample collection system and the needle 215. The biosample collection system comprises a biosample container 211, biosample connector 213, additive connector 217, additive container 219, flushing connector 254 and flushing container 223.

At least one container is disposed in the pump housing component space 93 near the second end 144 of the pump housing 14. As shown in FIG. 1, a preferred embodiment of the second end 144 of the pump housing 14 comprises a clear plastic container compartment 208 having a first end 210, a second end 212, an upper surface 214, a lower surface 216 and a container component space 218 formed therein which is part of the pump housing component space 93 and is sized to receive one or more containers. The container compartment 208 is secured to the second end 144 portion the pump housing 14 so that the upper 214 and lower surface 216 of the container compartment 208 are about flush respectively with the upper 138 and lower 38 surfaces of the second end 144 portion of the pump housing 14 and has the same general cross section as the second end 144 portion of the pump housing 14.

A biosample container 220 having a collection space 222 sized to receive at least one biosample is disposed in the second end 144 portion of the pump housing component space 93 and preferably in the container component space 218. The biosample container 220 must be able to withstand the suction pressure exerted by the pump. In a preferred embodiment, the biosample container 220 is an elastomeric sack. In another embodiment, the biosample container 220 is a molded flexible polyurethane compartment.

The collection space 222 of the biosample container 220 is in communication with the second end of the needle 16 so that a biosample collected by the needle 16 may be deposited in the collection space 222 of the biosample container 220. Preferably this communication is established by a biosample connector 228 having a first end 230, a second end 232, an outer periphery 233 and an opening (not shown) therethrough. In a preferred embodiment, the biosample connector 228 is elastomeric tubing.

The second end 232 of the biosample connector 228 is secured to a biosample container 220 so that the collection space 222 hereof is in communication with the opening in the biosample connector 228. The first end 230 of the biosample connector 228 is connected to the second end of the needle 16. As shown in FIG. 7, this connection may be accomplished by a conduit 236 having a first 238, second 240 and third 242 tubular projection extending therefrom thereby forming a T tubing. The terminal ends of the first, second, and third tubular projections have secured thereto respectively a first 244, second 246 and third 248 annular shoulder, having a first end 250 and a second end 252 wherein the second end 252 faces the conduit 236. There is an increase in size of the shoulder towards the conduit whereby the first end 250 of the shoulder has a smaller outside diameter than the second end 252 of the shoulder. The biosample connector 228 is sized to slide easily over the first end 250 of the shoulder 244 but must be forced over the second end 252 of the shoulder thereby securing the connector 228 to the tubular projection 238.

As previously described the second end of the needle 16 is in communication with the opening of the third shoulder 248 thereby establishing fluid communication between the first end 18 of the needle 16 and the collection space 222 in the biosample container 224. In a preferred embodiment, a flushing connector 254 is secured to the second shoulder 246 in the same manner as the first shoulder 244 to provide fluidic communication for the flushing substance to the biosample connector 228 as described hereafter. Another embodiment shown in FIG. 1 eliminates the need for the T tubing by fusing the flushing connector 254 to the biosample connector.

The first end 230 portion of the biosample connector 228 is positioned in the first biosample canal 258 of the pump housing component space 93 (FIG. 3) and follows the first back wall 166 of the rod support member component space 158. The second end 232 portion of the biosample connector 228 is positioned in the second biosample canal 260 which leads to the pump housing second end 144 portion containing the biosample container 220. The space between the first back wall 166 of the rod support member space 158 and the rods 198 is less than the diameter of the biosample connector 228 so that positioning the biosample connector 228 in this space permits the rotating rods 198 of the rod support member 160 to compressingly engage the biosample connector 228 as in FIG. 7 thereby creating a suction therein.

Figure 8:
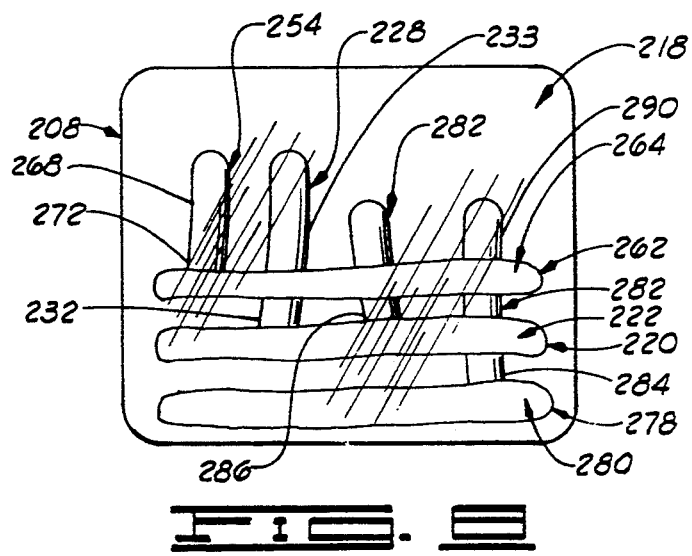
FIG. 8 is an elevational view of the second end of the pump housing of the present invention showing the clear plastic container compartment with connectors attached to the containers.

As shown in FIGS. 1 and 8, a flushing container 262 is positioned in the container compartment component space 218 and has a flushing substance space 264 formed therein sized to retain an effective amount of a flushing substance such as sterile normal saline solution. The flushing container 262 is preferably made from the same material as the biosample container 220.

A flushing connector 254 having an outer periphery 268, a first end 270 and a second end 272 with a connector opening (not shown) formed therethrough is shown in FIGS. 1 and 7. The second end 272 of the flushing connector 254 is connected to the flushing container 262 so that the flushing connector opening is in fluid communication with the flushing substance contained in the flushing container 262. In the preferred embodiment shown in FIG. 7, the first end 270 of the flushing connector 254 is secured to the second tubular projection 240 as previously described so that the flushing connector opening is in fluid communication with the biosample connector opening (not shown). In the preferred embodiment shown in FIG. 1 the first end 270 of the flushing connector 254 is fused at approximately a 30° angle to the biosample connector 228 to establish fluidic communication therebetween. Preferably the flushing connector is elastomeric tubing.

The second end 272 portion of flushing connector 254 is positioned in the first flushing canal 276 and contactingly follows the first front wall 162 to the second flushing canal 256. The space between the first front wall 162 and the outer periphery 202 of the rod cylinders 200 is larger than the diameter of the flushing connector 254 so the flushing connector 254 is not engaged by the rods 198 (FIG. 7). The flushing substance within the flushing container 262 is aspirated through the flushing connector opening by the suction created in the biosample connector 228 in communication therewith. The flow of the flushing substance is interrupted by selectively compressing the flushing connector 254 with the outer periphery 128 of the control member cylinder 126 as shown in FIG. 7 and as previously described.

A third container may be disposed in the second end 144 portion of the pump housing component space 93 which contains an additive. The additive container 278 comprises an additive space 280 formed therein sized to retain an effective amount of additive and is preferably made from the same material as the biosample container 220. The additive container 278 is in communication with an additive connector 282 having a first end 284 and a second end 286 with an opening (not shown) therethrough and an outer periphery 290. Preferably the additive connector is elastomeric tubing.

The first end 284 of the additive connector 282 is secured to the additive container 278 and the second end 286 of the connector 282 is secured to the biosample container 220 or a portion of the biosample connector 228 near the biosample container 220 so that the additive is in communication with the collection space 222 of the biosample container 220. The additive preferably does not enter the biosample connector 228 in a manner which could inadvertently contaminate the biosite with additive.

The first end 284 portion of the additive connector 282 is positioned in the lower additive canal 300 (FIG. 4.) and follows the second front wall 164, the side wall 169 and the second back wall 168 of the rod support member space 158 and into the upper additive canal 312 which leads to the biosample container 220. The space between the rods 198 and the walls of the rod support member space 158 is smaller than the diameter of the additive connector 282 so that the rotating rods 198 contact the additive connector 282 as shown in FIG. 7 creating a vacuum therein.

Figure 20:
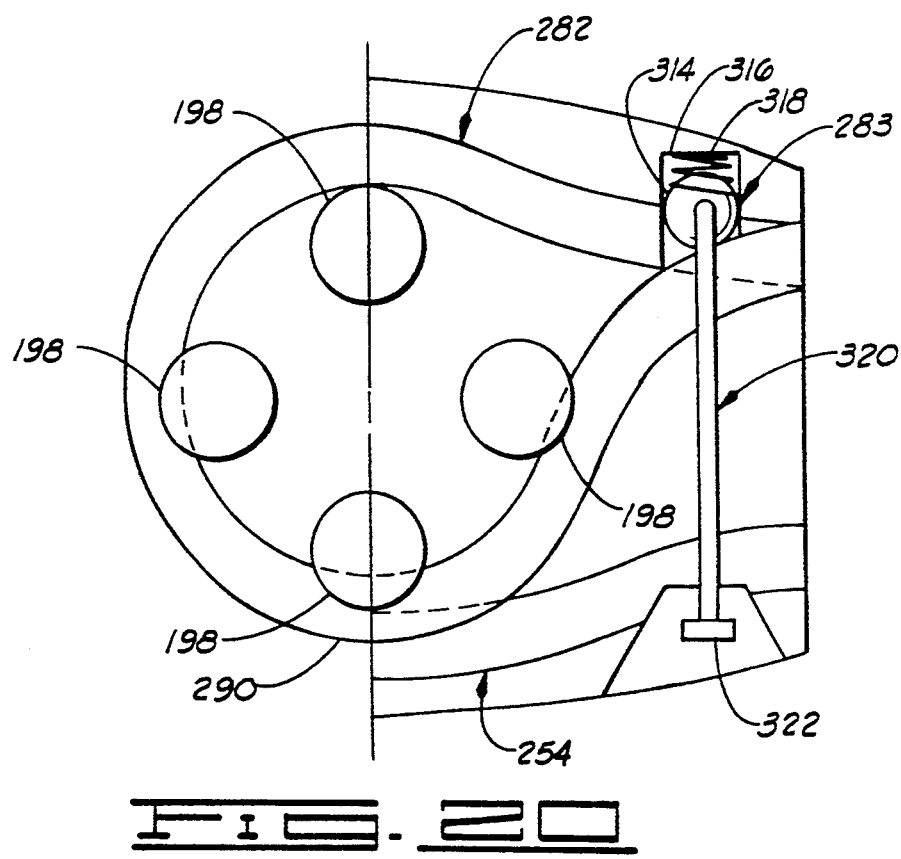
FIG. 20 is a top plan view of a horizontal cross section of the peristaltic pump with the additive connector and the additive regulator.

Referring to FIG. 20, the flow of the additive through the additive connector 282 can be regulated by an additive regulator generally designated by the numeral 283 which selectively compresses at least a portion of the additive connector 282. A ball 314 is disposed in the pump housing component space 93 near the upper additive canal 312 so that the ball compresses the additive connector 282. Between the ball 314 and the inside wall of the pump housing 316, preferably in a recessed area, is disposed a ball spring 318. A ball rod 320 is secured at one end to the ball 314 and extends a distance from the pump housing 14 at the opposite end. An additive button 322 is secured to the end of the ball rod 320 which extends from the pump housing 316. When the additive is desired in the biosample container 220, the additive button 322 is pressed which extends the ball rod 320 thereby displacing the ball 314 from the compressed additive connector 282 which permits the flow of the additive therethrough. When the additive button 322 is no longer pressed the ball spring 318 resiliently returns to a decompressed positioned which pushes the ball onto the additive connector 282 compressing same.

As previously described, a commercially available needle may be used with the aspirator of the present invention. Alternately, the following needles may be utilized.

The flushing needle shown in FIG. 16 and generally designated by the numeral 324, comprises a first shaft 325 having a first end 326 capable of cutting and receiving a biosample, a second end 328 attachable to a needle receiving member 329 such as the aspirator of the present invention, a duct 330 having a first end 331 and a second end 333 intersecting the first 326 and the second ends 328 of the first shaft 325. The first shaft 325 is capable of receiving an effective amount of flushing substance such as sterile normal saline solution in the first end 331 portion of the duct 330. In a preferred embodiment flushing substance is supplied to the first end 331 portion of the duct 330 by telescoping a second shaft 335 over the first shaft 325. The second shaft 335 comprises a first end 337 and a second end 339 secured to the first shaft 325 and a flushing substance space 341 formed between the first end 336 and the second end 339 of the second shaft 335. Flushing substance received by the flushing substance space 341 is received in the first end 331 portion of the duct 330 via a port 332 in the first end portion of the first shaft 325.

FIG. 16 shows a flushing solution reservoir attached to a second shaft port 338 positioned near the second end portion 339 of the second shaft 335; a valve 336 regulates the flow of flushing substance therebetween. The flushing solution is received in the flushing substance space 341 which is then received in the first end 331 portion of the duct 330 via port 332. A portion of the flushing solution is received at the biosite from the duct 330. A biosample is received by the first end 331 of the duct 330 and the flushing solution aids in the delivery of the biosample to the second end 333 thereof. Providing flushing substance to the first end portion of the duct and the biosite aids in obtaining and transferring biosamples from the biosite to a needle receiving member 329.

The obturator needle shown in FIG. 17 and generally designated by the numeral 340, comprises a shaft 343 having first end 342 capable of cutting and receiving a biosample, a second end 344 attachable to a needle receiving member 329 such as the aspirator of the present invention and an opening 346 intersecting the first end 342 and the second end 344 of the shaft 343. An obturator 348 having a first end 350 and a second end 352 is disposed in the opening 346 so that the obturator first end 350 blocks the opening of the first end 342 of the shaft 343. The opening 346 near the first end 342 of the shaft 343 is tapered and sized slightly larger that the diameter of the obturator 348. The remainder of the opening 346 is larger and sized to receive the obturator 348 and a biosample received by the first end 342 of the shaft 340. The second end 352 of the obturator 354 is attached to a means for withdrawing the obturator 354 a distance from the shaft first end 342 past the tapered portion of the opening 346 so that a biosample can be received by the needle first end 342 of the shaft 343. The withdrawing means is shown as an obturator trigger 354 in FIG. 17. The obturator needle 340 is used when several layers of tissue must be punctured before reaching the biosite. The obturator 348 prevents obtaining unwanted tissue samples until the first end of the needle is positioned at the biosite.

The flange needle shown in FIG. 18 and generally designated by the numeral 356 comprises a shaft 357 having a first end 358 capable of cutting and receiving a biosample, a second end 360 attachable to a needle receiving member 329 such as the aspirator of the present invention, an opening (not shown) intersecting the first 358 and the second 360 ends and an outer periphery 364. A flange member 366 is secured to the outer periphery 364 at a selected position in order to prevent further insertion of the needle 356 into a biosite. In operation, the first end 358 of the shaft 357 is inserted into the biosite such as a prostate gland. The flange member 366 acts as a guide to the operator to determine how far the shaft 357 has been inserted, and prevents a further insertion of the shaft 357 into an area past the prostate gland which could recover a biosample from an unintended biosite. Preferably the flange member 366 is made from the same material as the needle 356 and may be any shape which is large enough to form a stop surface in order to prevent inadvertent insertion into the patient. In a preferred embodiment for use in prostate gland, the flange member 366 is positioned 1.5 inches from the first end 358 of the shaft 357.

In one operation, the first end 18 of the needle 16 is positioned at the desired biosite such as a prostate gland. The first end 18 of the needle 16 cuttingly engages the prostate gland thereby receiving a tissue biosample in the opening of the first end thereof. The trigger 56 is pressed which activates the pump thereby establishing a vacuum capable of continuous vacuum directly in the biosample connector 228 and indirectly in the needle opening. The biosample is aspirated through the needle opening, through the biosample connector 228 and into the collection space 222 in the biosample container 220.

Pressing the trigger 56 moves the control member 124 thereby permitting the flushing substance to be aspirated through the flushing connector 254 by the suction created in the biosample connector 228 by the pump. The flushing substance is delivered to the biosample connector 228 and aids in the delivery of the biosample to the collection space 222 by flushing the biosample into same.

When the trigger 56 is pressed by the operator, the pump creates a suction in the additive connector 282. The additive button 322 is pressed thereby decompressing the additive connector 282 which permits the transfer of the additive to the biosample container. The additive may be any agent which aids in preserving, treating or analyzing the biosample. The present invention is especially useful if the additive or additives can identify a condition in the biosample which aids in the immediate diagnosis of the patient. This would eliminate the time and expense of the biosample being analyzed in the laboratory or for the pathologist to be present in the operating room.

After the first biosample is delivered to the collection space 222, multiple biosamples may be obtained by repositioning the first end 18 of the needle 16 to obtain the next desired biosample and repeating the previously described procedure. After the desired biosample or biosamples have been obtained, the trigger is returned to the off position and the aspirator withdrawn from the biosite. The pump housing 14 is snapped off and sent to the laboratory for appropriate analysis of the biosample or the biosample is viewed through the clear plastic container compartment for the appropriate response. A new pump housing 14 is snapped on the handle housing 12 to obtain the next biosample.

In the laboratory the pump housing 14 containing the biosamples is snapped onto a handle housing 12 having a reverse motor position. The reverse motor position is engaged and the biosamples are aspirated from the biosample container 220, through the biosample connector 228 and needle 16 and into a container for analysis. Thus laboratory personnel need never touch the biosample.

Changes may be made in the construction and operation of the various parts, elements and assemblies described herein and in the steps or in the sequence of steps of the methods described herein without departing from the spirit and scope of the invention as defined in the following claims.

What is claimed is:

1. A flushing needle for use with a needle receiving member wherein a portion of the needle receives flushing substances from a flushing substance reservoir and delivers a portion of the flushing substance to a biosample extracted from a biosite in a subject, comprising:

a first shaft comprising a first end characterized by a tip capable of extracting a biosample from the biosite, a second end attachable to the needle receiving member, and a duct having a first end and a second end, said duct extending through both the first end and the second end of the first shaft, the first end of the duct and the second end of the duct in corresponding alignment with and extending through both the first end and the second end of the first shaft, said duct being capable of containing a biosample;

a second shaft having a first end and a second end, the first end of the second shaft connected to the first shaft near the first end thereof, the second end of the second shaft adapted to be connected to the needle receiving member, a flushing substance space formed between the first shaft and the second shaft, the second shaft telescoped over and enclosing a substantial portion of the first shaft via an airtight connection of the second shaft to the first shaft, wherein both the first shaft and the second shaft comprise means for receiving a flushing substance;

means for delivering an effective amount of the flushing substance to the duct in the first shaft such that a biosample contained within said duct is contacted by said flushing substance; and means for causing a suction to be formed within the duct in the first shaft thereby causing both a biosample and said flushing substance contained within said duct to be moved toward the needle receiving member.

2. The flushing needle of claim 1 wherein the means for delivering an effective amount of a flushing substance comprises:

a port in the first end of the first shaft sized to receive an effective amount of a flushing substance in the first end of the duct, wherein flushing substance receiving in the flushing substance space is then received into the duct via the port in the first shaft; and means for delivering an effective amount of flushing substance from a flushing substance reservoir to the flushing substance space.

* * * * *

UNITED STATES PATENT AND TRADEMARK OFFICE
CERTIFICATE OF CORRECTION

PATENT NO. : 5,387,191
DATED : February 7, 1995
INVENTOR(S) : Hemstreet et al.

It is certified that error appears in the above-indentified patent and that said Letters Patent is hereby corrected as shown below:

Column 1, line 40, after the word "present" please insert -- invention --.

Column 3, line 2, please delete "a upper" and substitute therefor -- an upper --.

Column 4, line 37, please delete "control member opening 122" and substitute therefor -- control member opening 120 --.

Column 5, line 12, please delete "aluer" and substitute therefor -- a luer --.

Column 5, line 29, please delete "pump components space" and substitute therefor -- pump housing component space --.

Column 7, line 7, after the word "portion" please insert -- of --.

UNITED STATES PATENT AND TRADEMARK OFFICE
CERTIFICATE OF CORRECTION

PATENT NO. : 5,387,191
DATED : February 7, 1995
INVENTOR(S) : Hemstreet et al.

It is certified that error appears in the above-indentified patent and that said Letters Patent is hereby corrected as shown below:

Column 7, line 59, please delete "biosample container 224" and substitute therefor -- biosample container 220 --.

Column 10, line 29, please delete "shaft 340" and substitute therefor -- shaft 343 --.

Column 12, line 47, please delete "receiving" and substitute therefor -- received --.

Signed and Sealed this

Thirteenth Day of June, 1995

Attest:

BRUCE LEHMAN

Attesting Officer     Commissioner of Patents and Trademarks